United States Patent [19]
Wagner et al.

[11] Patent Number: 5,359,118
[45] Date of Patent: Oct. 25, 1994

[54] PROCESS FOR THE CONTINUOUS PREPARATION OF DIALKYL CARBONATES

[75] Inventors: Paul Wagner; Franz-Josef Mais, both of Duesseldorf; Hans-Josef Buysch, Krefeld; Reinhard Langer, Krefeld; Alexander Klausener, Cologne, all of Fed. Rep. of Germany

[73] Assignee: Bayer Aktiengesellschaft, Leverkusen, Fed. Rep. of Germany

[21] Appl. No.: 59,489

[22] Filed: May 10, 1993

[30] Foreign Application Priority Data

May 15, 1992 [DE] Fed. Rep. of Germany ....... 4216121

[51] Int. Cl.$^5$ .............................................. C07C 69/96
[52] U.S. Cl. ............................... 558/277; 203/DIG. 6
[58] Field of Search .......................................... 558/277

[56] References Cited

U.S. PATENT DOCUMENTS

| | | | |
|---|---|---|---|
| 4,181,676 | 1/1980 | Buysch et al. | 558/277 |
| 4,307,032 | 12/1981 | Krimm et al. | 558/277 |
| 4,691,041 | 9/1987 | Duranleau et al. | 558/277 |
| 5,231,212 | 7/1993 | Buysch et al. | 558/277 |

FOREIGN PATENT DOCUMENTS

| | | |
|---|---|---|
| 0530615 | 3/1993 | European Pat. Off. . |
| 2740243 | 3/1979 | Fed. Rep. of Germany . |
| 2740251 | 3/1979 | Fed. Rep. of Germany . |

*Primary Examiner*—Robert W. Ramsuer
*Assistant Examiner*—Michael G. Ambrose
*Attorney, Agent, or Firm*—Sprung Horn Kramer & Woods

[57] ABSTRACT

Di-($C_1$–$C_4$-alkyl) carbonates can be prepared by catalysed counter-current reesterification of ethylene glycol carbonate or propylene glycol carbonate with a $C_1$–$C_4$-alcohol in a column, ethylene glycol carbonate or propylene glycol carbonate being introduced into the upper part of the column and a dialkyl carbonate-containing $C_1$–$C_4$-alcohol being introduced into the central or lower part of the column and pure alcohol being additionally introduced below the introduction of the dialkyl carbonate-containing alcohol.

17 Claims, 3 Drawing Sheets

PROCESS FOR THE CONTINUOUS PREPARATION OF DIALKYL CARBONATES

BACKGROUND OF THE INVENTION

1. Field of the Invention

The present invention relates to a continuous process for the preparation of lower dialkyl carbonates by catalysed reesterification of ethylene glycol carbonate or propylene glycol carbonate with lower alcohols, the reaction of the alkylene carbonate with a dialkyl carbonate-containing alcohol being performed in counter-current. The process requires the introduction of pure alcohol below the point of introduction for the dialkyl carbonate-containing alcohol.

2. Description of the Related Art

The preparation of dialkyl carbonates from ethylene glycol carbonate and alcohols, in which the underlying ethylene glycol is formed simultaneously, is known and has been described repeatedly. However, almost all descriptions are concerned with the catalysis of this reesterification, while the industrial realisation of this process is not described in detail. However, in U.S. Pat. No. 4,691,041 as one of the few sources, there is a detailed description of such a process:

Ethylene glycol carbonate and methanol in a molar ratio of 1:4 are pumped at about 100° C. and about 7 bar through a tube filled with a basic ion exchanger, in the most expedient case the reesterification equilibrium being established, which contains, in addition to methanol as the main component and unreacted ethylene glycol carbonate, the reaction products dimethyl carbonate and ethylene glycol and additionally by-products, such as polyglycols and dimethyl ether.

The reaction mixture described is then separated in a first distillation apparatus into the high-boiling fractions ethylene glycol carbonate, ethylene glycol and polyglycols on the one hand and the low boilers methanol, dimethyl carbonate and dimethyl ether on the other hand. In a second distillation, the high boilers are separated into an ethylene glycol containing up to 10% of ethylene glycol carbonate and a polyglycol-containing ethylene glycol carbonate. The polyglycol-containing ethylene glycol carbonate flows back into the reesterification reaction, where the risk of concentration of the high-boiling by-products must be expected. The ethylene glycol carbonate-containing glycol is fed into a hydrolysis in which the glycol carbonate which has reached the ethylene glycol is cleaved into glycol and $CO_2$ and is thus lost as a source of carbon dioxide.

From the low-boiler fraction mentioned, in a 3rd distillation which is carried out at elevated pressure, a bottom phase of pure dimethyl carbonate and a dimethyl carbonate-depleted methanol, which additionally contains dimethyl ether, is then obtained. The dimethyl carbonate-containing methanol is likewise returned to the reesterification reaction. By the recycling of carbonate-containing material, the space-time yield of re-esterification product is markedly reduced. This reduction is estimated to be 30 to 40%, compared with the initial filling of the reesterification apparatus. This reduction is all the more painful, since in any case the best which can be expected is the establishment of the reesterification equilibrium. These reductions are extremely restrictive for an industrial implementation. Therefore, although the return of a dialkyl carbonate-containing alcohol appeared to be highly desirable, since in such a case an extensive, and thus expensive in terms of energy, separation of the dialkyl carbonate and the fundamental alcohol would not have to be carried out, such a return did not appear to be realisable. The avoidance of such an expensive separation of carbonate and alcohol is desirable to the same extent for all lower alcohols ($C_1$–$C_4$); however, it is particularly desirable in the dimethyl carbonate/methanol system which forms an azeotrope which is difficult to separate.

The use of a dialkyl carbonate-containing alcohol in an industrial realisation is nevertheless surprisingly expediently possible if the reesterification is carried out in a column apparatus in counter-current, a dialkyl carbonate-containing alcohol stream being led from the bottom towards the alkylene carbonate delivered in the upper part of the column, pure alcohol being additionally introduced below the introduction of the dialkyl carbonate-containing alcohol.

SUMMARY OF THE INVENTION

A process has been found for the continuous preparation of dialkyl carbonates of the formula

$$(R^1O)_2CO \qquad (I)$$

in which $R^1$ signifies straight-chain or branched $C_1$–$C_4$-alkyl, preferably methyl or ethyl, particularly preferably methyl,
by catalysed reesterification of ethylene glycol carbonate or propylene glycol carbonate, preferably of ethylene glycol carbonate, with an alcohol of the formula

$$R^1OH \qquad (II)$$

in which $R^1$ has the above meaning,
which is characterised in that the reesterification is carried out in a column in counter-current in such a manner that ethylene glycol carbonate or propylene glycol carbonate is introduced into the upper part of the column and a dialkyl carbonate-containing alcohol, whose dialkyl carbonate content is 0.2 to 30% by weight, preferably 1 to 28% by weight, particularly preferably 3 to 25% by weight, is introduced into the central or lower part of the column and pure alcohol is additionally introduced below the introduction of the dialkyl carbonate-containing alcohol.

DETAILED DESCRIPTION OF THE DRAWINGS

Figure 1:
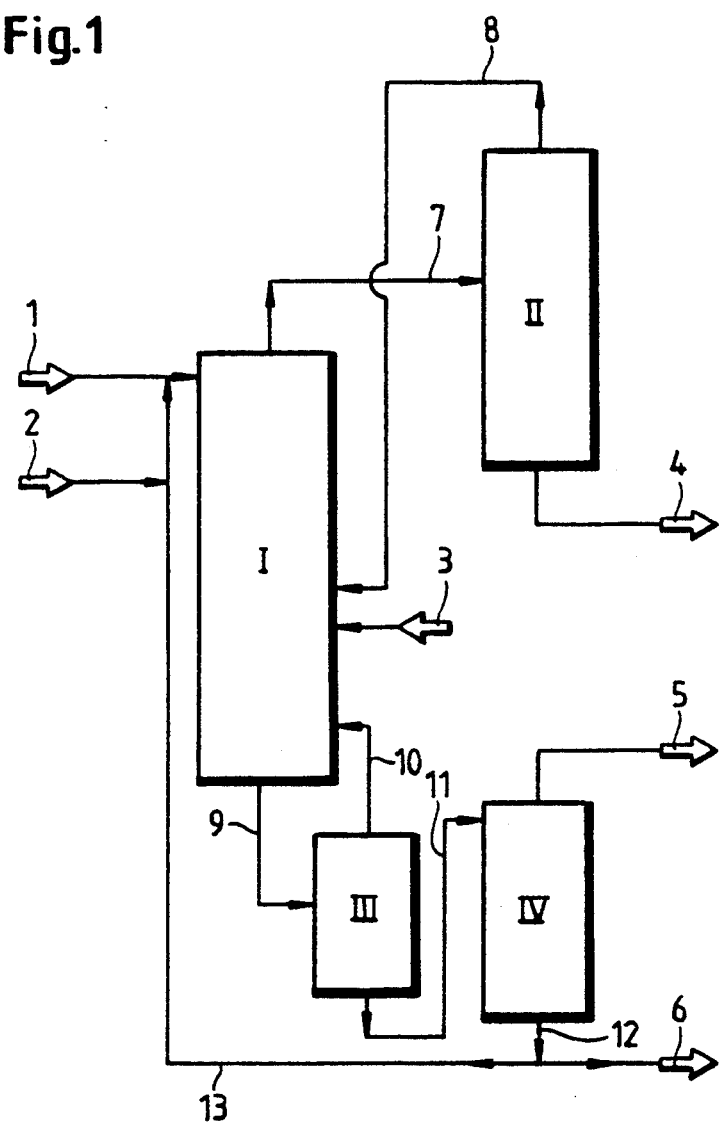

In FIG. 1 to FIG. 5 some variants and details of the inventive process are shown which are more fully explained below.

DETAILED DESCRIPTION OF THE INVENTION

The starting materials for the process according to the invention are accordingly ethylene glycol carbonate or propylene glycol carbonate, preferably ethylene glycol carbonate on the one hand and a lower alcohol, such as methanol, ethanol, propanol, isopropanol, butanol or isobutanol, on the other, which is associated with the concomitant di-($C_1$–$C_4$-alkyl) carbonate. In such a mixture, the proportion of the dialkyl carbonate is 0.2 to 30% by weight, preferably 1 to 28% by weight, particularly preferably 3 to 25% by weight, based on the total amount of dialkyl carbonate and the underlying alcohol. The alcohol to be used is preferably methanol or ethanol, particularly preferably methanol; correspondingly, the dialkyl carbonate associated with the alcohol is dimethyl carbonate or diethyl carbonate, preferably dimethyl carbonate.

The alkylene glycol carbonate, according to the invention, is fed into the upper part of the reesterification column. The alcohol containing the concomitant dialkyl carbonate is introduced into the central or lower part of the column; in the process according to the invention, pure alcohol of the same type is additionally introduced, below the point for feeding in the alcohol containing the concomitant dialkyl carbonate.

The alcohol containing the concomitant dialkyl carbonate and the pure alcohol are preferably introduced in the gaseous state and led towards the alkylene carbonate trickling down from above.

The reaction products of the process according to the invention are ethylene glycol or propylene glycol, preferably ethylene glycol, which is obtained as a bottom product and is supplied to a further purification. Furthermore, the desired dialkyl carbonate is obtained as a reaction product at the head of the column, generally in a mixture with the fundamental alcohol present in excess and not completely reacted. The desired dialkyl carbonate is isolated by distillation from this mixture withdrawn as head product. In this isolation, the fundamental alcohol to be separated off is produced in pure form only with great effort, in the specific case of the dimethyl carbonate/methanol system, because of the azeotrope formation, only with extremely great effort. When less effort is expended on distillation, on the other hand, a mixture of the alcohol to be separated off together with the concomitant dialkyl carbonate is always obtained.

While the alcohol containing according to the invention the concomitant dialkyl carbonate can originate from any desired source (thus for example from the preparation of alkyl-aryl carbonate or diaryl carbonate, in the isolation of which a dialkyl carbonate/alcohol mixture is likewise produced). it is preferred according to the invention to use a dialkyl carbonate-containing alcohol such as is produced in the isolation of the desired dialkyl carbonates in the described process according to the invention with the expenditure of little effort on distillation.

In FIG. 1 to FIG. 5 various aspects of the process according to the invention are represented as follows:

FIG. 1 shows the following apparatus: a reesterification column (I), a distillation column (II) and thin film-/falling film evaporators (III) and (IV). FIG. 1 shows in addition the following starting materials: alkylene glycol carbonate (1), catalyst (solution) (2) and alcohol (3). FIG. 1 further shows as products: dialkyl carbonate (4), alkylene glycol (5) and catalyst-containing high-boiler fraction (6) to be further treated. FIG. 1 further shows as internal streams: a gaseous stream of an alcohol/dialkyl carbonate mixture (7), an alcohol-enriched alcohol/dialkyl carbonate mixture (8) which is returned towards (I), a glycol-containing bottom stream (9), low-boiler-containing fractions (10) from the bottom stream, such as alcohol still present and dialkyl carbonate still present, which are returned towards (I), catalyst-containing crude alkylene glycol (11) and a catalyst-containing high-boiler-containing fraction (12), some of which is ejected as such (6) and some of which is delivered to the head of (I) with the aim of catalyst recycling (13).

FIG. 1 therefore shows the variant already mentioned in which the dialkyl carbonate-containing alcohol to be used according to the invention is an alcohol such as is produced in the isolation of the desired dialkyl carbonate. (I) can be a column furnished with internals (bubble-cap trays, sieve trays etc.) known to those skilled in the art or a column filled with packings of the type known to those skilled in the art. (II) is a distillation column which is preferably operated at elevated pressure, for example at 4 to 15 bar, preferably at 6 to 12 bar and which can be operated under simplified conditions in terms of apparatus and energy use (low reflux ratio). (III) and (IV) are of a generally known type. The re-esterification catalysts which can be used according to the invention are those known to those skilled in the art, for example hydrides, oxides, hydroxides, alcoholates, amides or salts of alkali metals, such as lithium, sodium, potassium, rubidium and caesium, preferably salts of lithium, sodium and potassium, particularly preferably salts of sodium and potassium (U.S. Pat. Nos. 3,642,858, 3,803,201, EP 1082). When the alcoholates are used, according to the invention these can also be formed in situ by the use of the elementary alkali metals and the alcohol to be reacted according to the invention. Salts of the alkali metals can be those of organic or inorganic acids, such as of acetic acid, propionic acid, butyric acid, benzoic acid, stearic acid, carbonic acid (carbonates or hydrogen carbonates), of hydrochloric acid, hydrobromic or hydroiodic acid, nitric acid, sulphuric acid, hydrofluoric acid, phosphoric acid, prussic acid, thiocyanic acid, boric acid, stannic acid, $C_1$-$C_4$-stannonic acids or antimonic acids. The compounds of the alkali metals in question are preferably the oxides, hydroxides, alcoholates, acetates, propionates, benzoates, carbonates and hydrogen carbonates, particularly preferably, hydroxides, alcoholates, acetates, benzoates or carbonates are used.

Such alkali metal compounds (possibly formed in situ from the free alkali metals) are used in amounts of 0.001 to 2% by weight, preferably 0.005 to 1.5% by weight, particularly preferably 0.01 to 1.0% by weight, based on the reaction mixture to be reacted.

It is possible according to the invention, if desired, to add complexing agents to such alkali metal compounds (EP 274 953). Examples which may be mentioned are crown ethers such as dibenzo-18-crown-6, polyethylene glycols or bicyclic nitrogen-containing cryptands.

Such complexing agents are used in amounts of 0.1 to 200 mol %, preferably in 1 to 100 mol %, based on the alkali metal compound.

Suitable catalysts for the process according to the invention are, in addition, thallium I compounds and thallium III compounds, such as the oxides, hydroxides, carbonates, acetates, bromides, chlorides, fluorides, formates, nitrates, cyanates, stearates, naphthenates, benzoates, cyclohexylphosphonates, hexahydrobenzoates, cyclopentadienylthallium, thallium methylate, thallium ethylate, preferably Tl-(I) oxide, Tl-(I) hydroxide, Tl-(I) carbonate, Tl-(I) acetate, Tl-(III) acetate, Tl-(I) fluoride, Tl-(I) formate, Tl-(I) nitrate, Tl-(I) naphthenate and Tl-(I) methylate (EP 1083). The amounts of thallium catalyst are not particularly critical. They are generally 0.0001–10% by weight, preferably 0.001–1% by weight, based on the total reaction mixture.

In the process according to the invention, in addition, nitrogen-containing bases can be used as catalysts (U.S. Pat. No. 4,062,884). Examples which may be mentioned are secondary or tertiary amines such as triethylamine, tributylamine, methyldibenzylamine, dimethylcyclohexylamine inter alia.

The amounts of the nitrogen-containing bases used according to the invention are from 0.01 to 10% by weight, preferably from 0.1 to 5% by weight, particularly preferably from 0.1 to 1% by weight, based on the total reaction mixture.

Catalysts which can additionally be used according to the invention are compounds selected from the group comprising phosphines, stibines, arsines or divalent sulphur compounds and selenium compounds and onium salts thereof (EP 180 387, U.S. Pat. No. 4,734,519). The following examples may be mentioned: tributylphosphine, triphenylphosphine, diphenylphosphine, 1,3-bis-(diphenylphosphino)propane, triphenylarsine, trimethylarsine, tributylarsine, 1,2-bis-(diphenylarsino)ethane, triphenylantimony, diphenylsulphide, diphenyldisulphide, diphenylselenide, tetraphenylphosphonium halide (Cl, Br, I), tetraphenylarsonium halide (Cl, Br, I), triphenylsulphonium halide (Cl, Br) etc.

The amounts of this catalyst group to be used according to the invention are in the range from 0.1 to 10% by weight, preferably from 0.1 to 5% by weight, particularly preferably in the range from 0.1 to 2% by weight, based on the total reaction mixture.

Furthermore, complexes or salts of tin, of titanium or of zirconium (U.S. Pat. No. 4,661,609) can be used according to the invention. Examples of such systems are butylstannonic acid, tin methoxide, dimethyltin, dibutyltin oxide, dibutyltin dilaurate, tributyltin hydride, tributyltin chloride, tin(II) ethylhexanoates, zirconium alkoxides (methyl, ethyl, butyl), zirconium(IV) halides (F, Cl, Br, I), zirconium nitrates, zirconium acetylacetonate, titanium alkoxides (methyl, ethyl, isopropyl), titanium acetate, titanium acetylacetonate etc.

The amounts which can be used according to the invention are 0.1 to 10% by weight, preferably 0.5 to 5% by weight, based on the total mixture.

In the process according to the invention, furthermore, bifunctional catalysts of the formula

can be used. In these bifunctional catalysts, the molar ratio of the two components in square brackets is expressed by the indices m and n. These indices can, independently of each other, have values of 0.001–1, preferably 0.01–1, particularly preferably 0.05–1 and highly particularly preferably 0.1–1. Within the square brackets are neutral salts each composed of one cation and one anion. The indices a and b are, independently of each other, integers from 1–5; the indices c and d denote, independently of each other, integers from 1–3, where the valency requirements of the cations and anions for the formation of such neutral salts are to be complied with. Furthermore, in (III)

A denotes the cation of a metal which belongs to the
third period and group IIa, the
fourth period and group IIa, IVa–VIIIa, Ib or IIb, the
fifth period and group IIa, IVa–VIIa or IVb or the
sixth period and group IIa–VIa of the Periodic Table of the Elements in the short periodic form.

The metals considered for the cation A are taken by those skilled in the art from the conventional representations of the Periodic Table of the Elements (Mendeleev) in the short periodic form. Preferably, A is the cation of one of the metals Mg, Ca, Sr, Ba, Zn, Cu, Mn, Co, Ni, Fe, Cr, Mo, W, Ti, Zr, Sn, Hf, V and Ta, preferably the cation of one of the metals Mg, Ca, Zn, Co, Ni, Mn, Cu and Sn. Apart from the non-complexed cations of the metals mentioned, cationic oxo complexes of the metals mentioned are also considered, such as for example titanyl $TiO^{++}$ and chromyl $CrO_2^{++}$.

The anion X belonging to the cation A is that of an inorganic or organic acid. Such an inorganic or organic acid can be monobasic or dibasic or tribasic. Such acids and their anions are known to those skilled in the art. Examples of anions of monobasic inorganic or organic acids are: fluoride, bromide, chloride, iodide, nitrate, the anion of an alkanecarboxylic acid having 1–16 C atoms and benzoate; examples of anions of dibasic inorganic or organic acids are: sulphate, oxalate, succinate, fumarate, maleate, phthalate and others; examples of tribasic inorganic or organic anions are: phosphate or citrate. Preferred anions X in the catalyst of the formula (III) are: fluoride, chloride, bromide, iodide, sulphate, nitrate, phosphate, formate, acetate, propionate, oxalate, butyrate, citrate, succinate, fumarate, maleate, benzoate, phthalate, decanoate, stearate, palmitate and laurate. Particularly preferred anions X are: chloride, bromide, iodide, acetate, laurate, stearate, palmitate, decanoate, nitrate and sulphate.

Cation B in the catalysts of the formula (III) is selected from the group comprising the alkali metal cations or alkaline earth metal cations, the quaternary ammonium, phosphonium, arsonium or stibonium cations and the ternary sulphonium cations.

Alkali (alkaline earth) metal cations which may be mentioned in this context are: the cations of the group comprising lithium, sodium, potassium, rubidium, caesium, magnesium, calcium, strontium and barium, preferably the alkali metal cations mentioned, particularly preferably the sodium cation and the potassium cation.

Cations B considered are preferably those of the formulae

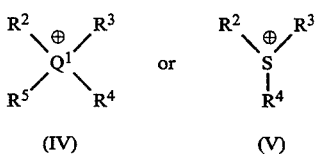

in which
Q¹ represents N, P, As or Sb and
R², R³, R⁴ and R⁵, independently of each other, straight-chain or branched $C_1$–$C_{18}$ or $C_7$–$C_{12}$-aralkyl and one of the radicals R²–R⁵ can also be $C_6$–$C_{12}$.

B is particularly preferably a cation of the formula

in which
Q² represents N or P, preferably N.

Highly particularly preferably, in the context of the formulae (IV) or (VI) the place of the radicals R², R³, R⁴ and R⁵ is taken by the radicals R¹², R¹³, R¹⁴ and R¹⁵, respectively, which, independently of each other, denote straight-chain or branched $C_1$–$C_{12}$-alkyl or $C_7$–$C_8$-aralkyl and one of the radicals R¹² to R¹⁵ can alternatively be phenyl. Furthermore, highly particularly preferably, the place of the radicals R¹², R¹³, R¹⁴ and R¹⁵ is taken by the radicals $R^{22}$, $R^{23}$, $R^{24}$ and $R^{25}$, respectively, which, independently of each other, denote $C_1$-$C_8$-alkyl or benzyl and one of the radicals $R^{22}$ to $R^{25}$ can alternatively be phenyl.

Straight-chain or branched $C_1$-$C_8$-alkyl is, for example, methyl, ethyl, propyl, isopropyl, butyl, isobutyl, hexyl, octyl, dodecyl, hexadecyl or octadecyl. A preferred alkyl has 1–12 C atoms, a particularly preferred alkyl has 1–8 C atoms.

$C_7$-$C_{12}$-Aralkyl is, for example, benzyl, phenylethyl, phenylpropyl, naphthylmethyl or naphthyl-ethyl; a preferred aralkyl is benzyl or phenylethyl, a highly particularly preferred aralkyl is benzyl.

$C_6$-$C_{12}$-Aryl is, for example, phenyl, naphthyl or biphenylyl, preferably phenyl.

The anion Y in the catalyst of the formula (III) is a halide ion, such as fluoride, chloride, bromide or iodide, preferably bromide or iodide, particularly preferably iodide. However, it can also represent other anions mentioned under X, if in the specific case the anion X is bromide or iodide.

The bifunctional catalyst of the formula (III) is used in an amount of 0.005–5% by weight, preferably 0.01–3% by weight, particularly preferably 0.01–1% by weight, based on the total reesterification mixture.

These catalyst amounts differ in part from the amounts mentioned in the literature. It is particularly surprising that, in the process according to the invention, relatively high concentrations of the active catalyst based on alkali metal compounds can be used without in this case the occurrence of the yield-reducing and reaction course-impeding developments of $CO_2$ and the formation of polyols, as is disclosed, for example, by German Offenlegungsschrift 2 740 243 and the literature cited therein and by German Offenlegungsschrift 2 740 251. This is also a surprising peculiarity of the process according to the invention.

Such catalysts can be applied to the head of the column homogeneously dissolved, solvents used being alkylene glycol carbonate, alkylene glycol, alcohol or dialkyl carbonate, that is solvents inherent in the system. It is, of course, possible to use insoluble reesterification catalysts which are arranged on the intermediate trays or in the middle of the packing of (I). In such a case, the metering of a dissolved catalyst via (2) can be dispensed with. Suitable heterogeneous catalysts are for example: ion exchanger resins having functional groups of tertiary amines, quaternary ammonium groups, where counter ions which may be mentioned as examples are hydroxide, chloride or hydrogen sulphate, sulphonic acid groups or carboxyl groups, where counter ions which may be mentioned for both as examples are hydrogen, alkali metals or alkaline earth metals. These functional groups can be bound to the polymer either directly or via inert chains (U.S. Pat. Nos. 4,062,884, 4,691,041, JA 63/238 043, EP 298 167). Furthermore, alkali metal silicates or alkaline earth metal silicates, impregnated on silicon dioxide supports, and ammonium-exchanged zeolites may be mentioned.

Figure 2:
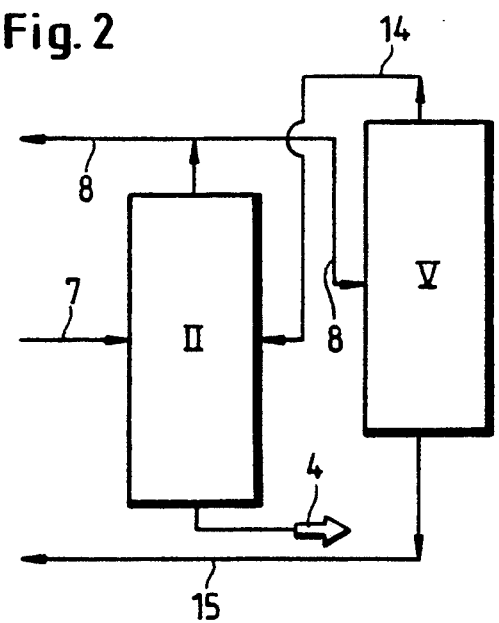

FIG. 2 shows a supplement and improvement to the separation of the head stream (7) of (I). In this case, as depicted in FIG. 1, pure dialkyl carbonate (4) is first separated off in (II) and a dialkyl carbonate-containing alcohol (8) is withdrawn in the gaseous state. (8), in a modification to FIG. 1, is now only partly (for example 30 to 80%, preferably 40 to 70%, of the total flow) directly returned towards (I), while the remainder is introduced into a second distillation column (V), roughly in the centre, and is there divided into a bottom stream (15) representing almost pure alcohol and a head stream (14) containing almost all of the dialkyl carbonate together with further alcohol. While (14) is returned for further recovery of dialkyl carbonate to (II), (15) is preferably used as the pure alcohol to be used according to the invention in (1) and there represents a part of (3).

Figure 3:
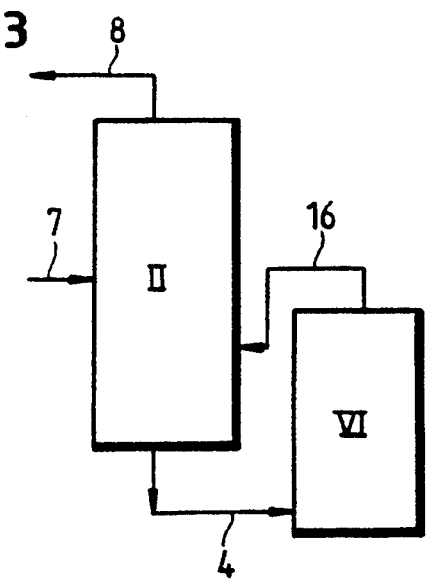

FIG. 3 shows a still further aspect of the process according to the invention, namely the coupling to the preparation of arylalkyl carbonate or diaryl carbonate, which is obtained by reaction of dialkyl carbonate with a phenol and in which a mixture of cleaved-off alcohol and incompletely reacted dialkyl carbonate (16) is formed. When (16) has a content of dialkyl carbonate in the range according to the invention of (8), such a stream can be used according to the invention instead of (8). However, according to FIG. 3, it is returned towards (II) for the recovery of the dialkyl carbonate and for the extensive separation of the fundamental alcohol.

Figure 4:
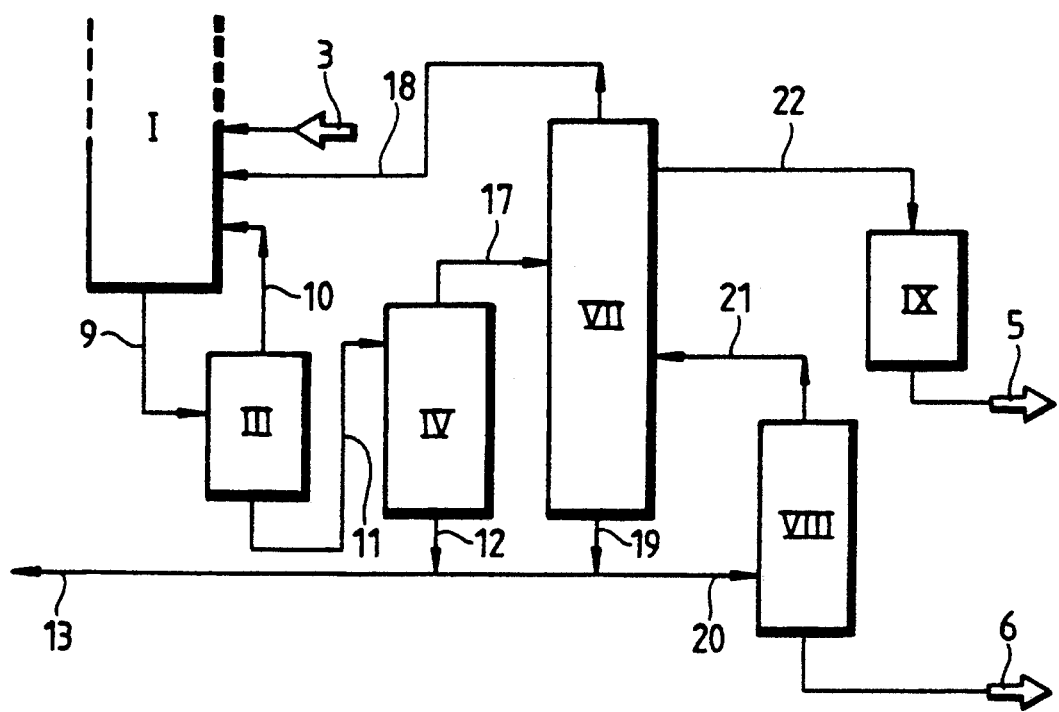

Finally, FIG. 4 shows a further preferred variant in the treatment of the bottom stream (9) for the recovery of the alkylene glycol produced according to the invention and for the further treatment of the high-boiler fraction (6). In this case, a glycol stream (17) is initially taken from (IV) and worked up in a further distillation column (VII) to give purified glycol (22) which can be worked-up as required in a further purification step (IX) (additional distillation, extraction or the like) to give pure glycol (V). (22) is withdrawn in the upper region of (VII) as a side-stream. A low-boiler stream (18) produced in (VII) is returned towards (I). Part of the high-boiler stream (19) produced in (VII) can, as in (12), be added to the return line (13), but is at least partly concentrated in (VIII) with respect to its content of high boilers, additional glycol (21) being produced. The concentrated bottom product of (VIII) is discharged as (6).

Figure 5:
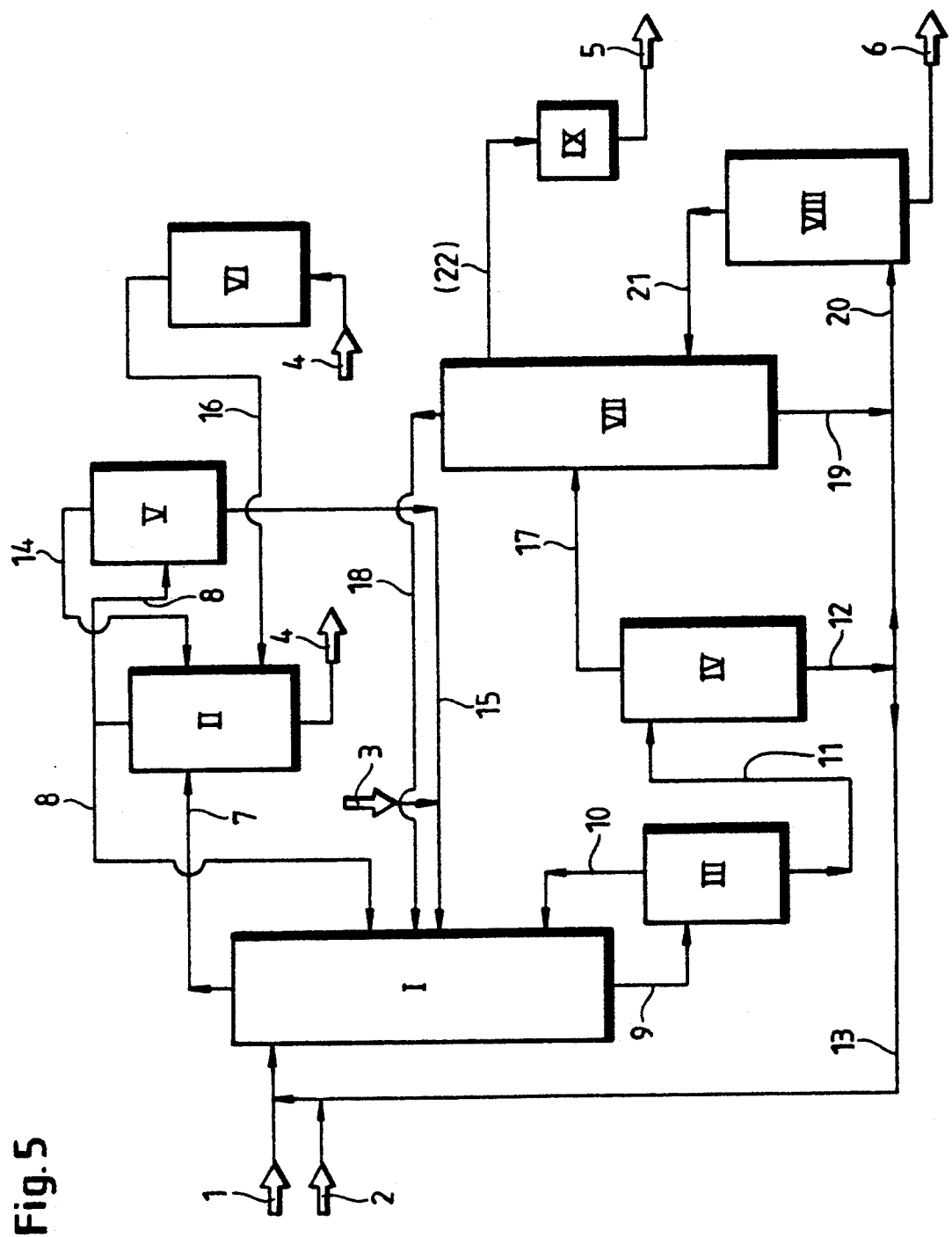

FIG. 5 shows an integrated process variant, in which the preferred elements of FIG. 2, FIG. 3 and FIG. 4 have been integrated in FIG. 1. All apparatus streams and mass streams are marked in FIG. 5 with the same reference signs as in FIG. 1 to FIG. 4.

The reesterification in (1) is carried out at 0.5 to 5 bar, preferably 0.8 to 1.5 bar, particularly preferably at atmospheric pressure and at a temperature of 40° to 150° C., preferably at 45° to 130° C.

The pure alcohol (3) or additionally (15) to be fed in according to the invention is 0.2 to 5 times the dialkyl carbonate fraction in the dialkyl carbonate-containing alcohol to be introduced via (8).

The head stream (7) withdrawn from (I) has, for example in the case of methanol/dimethyl carbonate, the composition of the azeotrope having 70% by weight of methanol and 30% by weight of dimethyl carbonate or has higher fractions of dimethyl carbonate.

The alcohol to be used as (3) can also be obtained from an alcohol/dialkyl carbonate mixture, from which the dialkyl carbonate has been isolated by pervaporation, vapour permeation or two-pressure distillation. The process according to the invention has the advantages below compared with the prior art disclosed by U.S. Pat. No. 4,691,041:

a) The establishment of equilibrium proceeds rapidly and leads to very high conversions and very high selectivities as a result of constantly altering composition.

b) As a result of the virtually complete reesterification of the alkylene carbonate, an alkylene glycol virtually free from alkylene carbonate is formed; the losses of alkylene carbonate, disclosed by the prior art (US'041), as a result of subsequent hydrolysis are avoided in this case.

c) As a consequence of short residence times, the formation of by-products, such as the formation of polyglycols, is restricted to amounts below 1%, based on the total amount of alkylene glycol.

d) The process according to the invention can be carried out using little apparatus, which can be assembled from standardised types.

e) In the preferred embodiment according to FIG. 1 to FIG. 5, many internal streams are not condensed, but are conducted as vapour-form streams. In this manner, the amounts of substance to be distilled are reduced and an energetically favourable procedure is created.

f) Coupling to the preparation of alkyl-aryl carbonates or diaryl carbonates is possible, which is expedient in terms of the process.

EXAMPLE

In an apparatus arrangement according to FIG. 5, a counter-current reesterification column (I) having a stripping part and an enrichment part was heated with the establishment of a temperature gradient in such a manner that the bottom temperature was about 120° C. and the head temperature was about 50° C. 367 g/h of ethylene glycol carbonate were metered in via (1). 872 g/h of a mixture of 80% by weight of methanol and 20% by weight of dimethyl carbonate were metered in via (8). Into the lower part of the column, but above the stripping part, 270 g/h of methanol were metered in via (3) and a further 130 g/h of methanol were metered in via (15). Furthermore, 37 to 38 g/h of a recycled bottom phase containing 4% by weight of catalyst (KOH) were metered in to the head of (I) via (13) and 1.2 g/h of fresh potassium hydroxide were metered in via (2). In as much as these metered-in mass streams represented internal mass streams, they were taken from the apparatuses indicated in FIG. 5.

The methanol-containing metered-in mass streams ascended the column in the vapour phase in the opposite direction to the descending liquid and catalyst-containing ethylene glycol carbonate, during which the reesterification to form dimethyl carbonate and ethylene glycol proceeded. 380 g/h of a mixture (7) of 60% by weight of methanol and 40% by weight of dimethyl carbonate were withdrawn from the head of (I), which was applied to the centre of a tray column (II) and was separated at a pressure of 10 bar into a mixture of roughly 80% by weight of methanol and 20% by weight of dimethyl carbonate and 378 g/h of dimethyl carbonate (4). Of the mixture (8) withdrawn in the vapour phase, the said 872 g/h were returned towards (I), while the remaining part of (8) was further separated in column (V); in this case a dimethyl carbonate-containing head product was obtained, which was returned towards (II) and 130 g/h of a bottom product (15) was obtained, essentially composed of methanol, which bottom product was returned towards (I).

The bottom product (9) of (I) which was essentially composed of ethylene glycol, small amounts of low boilers (methanol and dimethyl carbonate), high boilers, such as diethylene glycol and the catalyst, was passed into a falling film evaporator (III), from which 38 g/h of low boilers (10) were returned towards (I). 375 g/h of bottom product (11) were passed into a further falling film evaporator (IV), from which 75 g/h of concentrated catalyst solution (12) were withdrawn via its bottom, roughly half of which was returned via (13) towards (I) and the other half of which was metered into a thin film evaporator having a separating attachment (VIII). 302 g/h of vapour phase (17) from (IV) were metered into the column (VII). In (VII) 77 g/h of low boilers (18) were again isolated, which were returned towards (I). 255 to 256 g/h of glycol (22) were withdrawn as a side stream from the upper part of (VII), which, depending on purity requirements, could be further treated in (IX) to give highly pure glycol (5) at a rate of 255 g/h. The bottom effluent (19) of (VII), at a rate of 58 to 59 g/h, was, together with half of the bottom effluent (12) of (IV), fed to a thin film evaporator (VIII), the distillate (21) of which was supplied at a rate of 91 g/h to the bottom part of (VII). The concentrated bottom phase (6) of (VIII) containing all high boilers and a part of the catalyst was fed to further treatment.

What is claimed is:

1. A process for the continuous preparation of dialkyl carbonate of the formula $$(R^1O)_2CO,$$

in which $R^1$ signifies straight-chain or branched $C_1$–$C_4$-alkyl,
by catalysed reesterification of ethylene glycol carbonate or propylene glycol carbonate with an alcohol of the formula $$R^1OH,$$

in which $R^1$ has the above meaning,
wherein the reesterification is carried out in a column in counter-current in such a manner that ethylene glycol carbonate OF propylene glycol carbonate is introduced into the upper part of the column and a dialkyl carbonate-containing alcohol, whose dialkyl carbonate content is 0.2 to 30% by weight is introduced into the central or lower part of the column and pure alcohol is additionally introduced below the introduction of the dialkyl carbonate-containing alcohol.

2. The process of claim 1, wherein $R^1$ signifies methyl or ethyl.

3. The process of claim 2, wherein $R^1$ signifies methyl.

4. The process of claim 1, wherein ethylene glycol carbonate is reesterified.

5. The process of claim 1, wherein the dialkyl carbonate-containing alcohol has a dialkyl carbonate content of 1 to 28% by weight.

6. The process of claim 5, wherein the dialkyl carbonate containing alcohol has a dialkyl carbonate content of 3 to 25% by weight.

7. The process of claim 1, wherein the dialkyl carbonate-containing alcohol originates from the separation by distillation in a distillation column of the dialkyl carbonate/alcohol mixture withdrawn as head stream from the reesterification into dialkyl carbonate and a dialkyl carbonate-containing alcohol.

8. The process of claim 7, wherein the separation by distillation is carried out at 4 to 15 bar.

9. The process of claim 8, wherein the separation by distillation is carried out at 6 to 12 bar.

10. The process of claim 1, wherein the pure alcohol signifies 0.2 to 5 times the dialkyl carbonate fraction in the dialkyl carbonate-containing alcohol.

11. The process of claim 1, wherein the reesterification is carried out at a temperature of 40° to 150° C. and a pressure of 0.5 to 2 bar.

12. The process of claim 11, wherein the reesterification is carried out at a temperature of 45° to 130° C.

13. The process of claim 11, wherein the reesterification is carried out at a pressure of 0.9 to 1.2 bar.

14. The process of claim 1, wherein dimethyl carbonate is prepared by reesterification of ethylene glycol carbonate with methanol.

15. The process of claim 7, wherein 30 to 80% by volume of the further head stream, obtained in the separation by distillation of the dialkyl carbonate/alcohol mixture withdrawn as a head stream from the reesterification, is returned to the reesterification, while the remainder is fed to a further distillation, the bottom product of which is essentially composed of the alcohol and is returned to the lower part of the reesterification column, while the head product of this second column is returned to the first separation column (II).

16. The process of claim 15, wherein 40 to 70% by volume of the further herd stream is returned to the reesterification.

17. The process of claim 7, wherein an additional dialkyl carbonate/alcohol stream, originating from a process for the preparation of alkyl-aryl carbonate or diaryl carbonate, is supplied to the distillation column (II).

* * * * *

UNITED STATES PATENT AND TRADEMARK OFFICE
CERTIFICATE OF CORRECTION

PATENT NO. : 5,359,118
DATED : October 25, 1994
INVENTOR(S) : Paul Wagner, et al.

It is certified that error appears in the above-indentified patent and that said Letters Patent is hereby corrected as shown below:

Col. 10, line 40,      delete "OF" and substitute --or--

Col. 12, line 9,      delete "herd" and substitute --head--

Signed and Sealed this

Fifteenth Day of December, 1998

Attest:

BRUCE LEHMAN

*Attesting Officer*     Commissioner of Patents and Trademarks